United States Patent
Hallen

(10) Patent No.: US 11,045,353 B2
(45) Date of Patent: Jun. 29, 2021

(54) OPHTHALMIC SURGICAL SYSTEM WITH INFUSION FLUID AND SUBSTANCE DELIVERY THROUGH AN INFUSION CANNULA

(71) Applicant: Novartis AG, Basel (CH)

(72) Inventor: Paul R. Hallen, Colleyville, TX (US)

(73) Assignee: Alcon Inc., Fribourg (CH)

( * ) Notice: Subject to any disclaimer, the term of this patent is extended or adjusted under 35 U.S.C. 154(b) by 503 days.

(21) Appl. No.: 15/975,934

(22) Filed: May 10, 2018

(65) Prior Publication Data
US 2018/0338861 A1 Nov. 29, 2018

Related U.S. Application Data

(60) Provisional application No. 62/510,378, filed on May 24, 2017.

(51) Int. Cl.
| | | |
|---|---|---|
| A61F 9/007 | (2006.01) | |
| A61M 5/142 | (2006.01) | |
| A61M 5/14 | (2006.01) | |

(52) U.S. Cl.
CPC ......... *A61F 9/00736* (2013.01); *A61M 5/142* (2013.01); *A61M 5/1407* (2013.01); *A61M 5/1408* (2013.01); *A61M 2202/04* (2013.01); *A61M 2205/3337* (2013.01); *A61M 2205/50* (2013.01); *A61M 2205/502* (2013.01); *A61M 2210/0612* (2013.01)

(58) Field of Classification Search
CPC .............. A61F 9/00736; A61F 9/00745; A61F 9/00781; A61F 9/00763; A61F 9/0017; A61F 9/007; A61M 1/0058; A61M 1/0031; A61M 1/0062; A61M 1/0064; A61M 3/0233
See application file for complete search history.

(56) References Cited

U.S. PATENT DOCUMENTS

| | | | |
|---|---|---|---|
| 4,011,869 A | | 3/1977 | Seiler, Jr. |
| 4,199,307 A | * | 4/1980 | Jassawalla ........ A61M 5/14224 128/DIG. 12 |

(Continued)

FOREIGN PATENT DOCUMENTS

| | | |
|---|---|---|
| EP | 2838470 B1 | 6/2018 |
| WO | WO2015171189 A1 | 11/2015 |

OTHER PUBLICATIONS

Calhoun, et al., The Roto-Extractor in Pediatric Ophthalmology, Tr. Am. Ophth. Soc., vol. LXXIII, 1975, 14 pages.

(Continued)

*Primary Examiner* — Manuel A Mendez

(57) ABSTRACT

In some embodiments, an ophthalmic cassette valve may be configured to control flow of an infusion fluid and an ophthalmic substance (e.g., ophthalmic drug, a retina patch material, or an ophthalmic dye) to an infusion cannula. The valve may be configured to provide an alternating or mixed flow of the infusion fluid and the ophthalmic substance to the infusion cannula. In some embodiments, the cassette may include multiple substance chambers with different substances. The cassette may also include a one or more valves to control the flow to the infusion fluid (e.g., on/off for each of the substances and infusion fluid and/or a ratio of the substances and infusion fluid).

20 Claims, 8 Drawing Sheets

(56) References Cited

U.S. PATENT DOCUMENTS

| | | | |
|---|---|---|---|
| 5,562,612 | A | 10/1996 | Fox |
| 5,716,363 | A | 2/1998 | Josephberg |
| 5,989,262 | A | 11/1999 | Josephberg |
| 6,059,792 | A | 5/2000 | Josephberg |
| 6,203,296 | B1 * | 3/2001 | Ray .................. A61M 5/142 417/477.2 |
| 6,984,230 | B2 | 1/2006 | Scheller et al. |
| 7,214,210 | B2 * | 5/2007 | Kamen ............ A61M 5/14224 141/1 |
| 7,338,477 | B2 | 3/2008 | Meyer |
| 7,559,914 | B2 | 7/2009 | Domash |
| 7,717,129 | B2 | 5/2010 | Steppe |
| 7,871,399 | B2 | 1/2011 | Dacquay |
| 8,038,692 | B2 | 10/2011 | Valencia |
| 9,795,505 | B2 | 10/2017 | Yu |
| 2007/0000301 | A1 | 1/2007 | Todd |
| 2008/0208110 | A1 | 8/2008 | Sanchez |
| 2010/0331765 | A1 * | 12/2010 | Sullivan ................ A61M 11/06 604/24 |
| 2017/0165114 | A1 | 6/2017 | Hallen |
| 2017/0172694 | A1 | 6/2017 | Dos Santos |
| 2017/0172796 | A1 | 6/2017 | Biancalana |
| 2018/0338861 | A1 | 11/2018 | Hallen |

OTHER PUBLICATIONS

Douvas, Microsurgical Roto-Extractor Instrument for Vitrectomy, New Research on the Aetiology and Surgery of Retinal Detachment Mod. Probl. Ophthal., vol. 15, pp. 253-260 (Karger, Basel 1975), Port Huron, Michigan, USA.

* cited by examiner

OPHTHALMIC SURGICAL SYSTEM WITH INFUSION FLUID AND SUBSTANCE DELIVERY THROUGH AN INFUSION CANNULA

This application claims the benefit of priority of U.S. Provisional Patent Application Ser. No. 62/510,378 titled "OPHTHALMIC SURGICAL SYSTEM WITH INFUSION FLUID AND SUBSTANCE DELIVERY THROUGH AN INFUSION CANNULA", filed on May 24, 2017, whose inventor is Paul R. Hallen, which is hereby incorporated by reference in its entirety as though fully and completely set forth herein.

TECHNICAL FIELD

The present disclosure is directed to methods and systems for medical procedures, and more particularly, to methods and systems involving a need for delivering an ophthalmic substance into the eye through an infusion cannula.

BACKGROUND

Vitreo-retinal procedures are commonly performed to treat many serious conditions of the posterior segment of the eye. For example, vitreo-retinal procedures may treat conditions such as age-related macular degeneration (AMD), diabetic retinopathy and diabetic vitreous hemorrhage, macular hole, retinal detachment, epiretinal membrane, cytomegalovirus (CMV) retinitis, and many other ophthalmic conditions.

When performing vitreo-retinal procedures, a surgeon may use a microscope with special lenses designed to provide a clear image of the posterior segment of the eye. As access points, the surgeon may make several tiny incisions just a millimeter or so in diameter on the sclera at the pars plana. The surgeon inserts microsurgical instruments through the incisions, such as a fiber optic light source to illuminate inside the eye, an infusion conduit to maintain the eye's shape during surgery, and instruments to cut and remove the vitreous body. Conventionally, a separate incision may be provided for each microsurgical instrument when using multiple instruments simultaneously.

During such surgical procedures, proper illumination and visualization of the tissue to be treated or removed, such as vitreous, is important. Some vitreoretinal procedures require removal of the vitreous from the posterior segment of the eye. Because the vitreous is clear, visualization can be unusually difficult compared with some other types of tissues. In order to better visualize the clear vitreous, a dye may be introduced into the cavity of the eye. The dye adheres to the vitreous, which can then be seen more easily and, consequently, can be removed more easily.

In some instances, the dye (or another ophthalmic substance such as a drug or retina patch) may be introduced into the eye through an access cannula extending through the sclera. However, this may require either the removal of one of the tools being used in a given procedure or an additional incision in the eye. Either of these options results in increased surgical time and potential complications. Additionally, when a tool is removed and replaced after injection of the ophthalmic substance, if additional ophthalmic substance is needed (e.g., to better visualize remaining vitreous or to provide additional drug volume), the process of removal, injection, and replacement may need to be repeated.

SUMMARY

In some embodiments, an ophthalmic console may include a cassette that comprises a cassette infusion connector configured to receive infusion fluid from an infusion fluid system (such as a source of infusion fluid coupled to the console), a substance chamber comprising an ophthalmic substance (e.g., an ophthalmic drug, a retina patch material, or an ophthalmic dye), and at least one valve coupled to the cassette infusion connector and the substance chamber. In some embodiments, the at least one valve may be configured to control flow of the infusion fluid from the cassette infusion connector and control flow of the ophthalmic substance from the substance chamber to provide a flow to an infusion cannula fluidically coupled to the ophthalmic cassette. In some embodiments, the console or cassette may be coupled to a control mechanism configured to receive input from a user to use in controlling the at least one valve. In some embodiments, the at least one valve may be configured to provide a mixed flow of the infusion fluid and the ophthalmic substance to the infusion cannula. In some embodiments, the at least one valve may be configured to provide an alternating flow of the infusion fluid or the ophthalmic substance to the infusion cannula.

In various embodiments, the substance chamber may be a first substance chamber comprising a first ophthalmic substance and the cassette may further include a second substance chamber comprising a second ophthalmic substance. In some embodiments, the at least one valve may be configured to control flow of the infusion fluid from the cassette infusion connector, the first ophthalmic substance from the first substance chamber and the second ophthalmic substance from the second substance chamber to provide an alternative or mixed flow to the infusion cannula. In some embodiments, the at least one valve may comprise (a) a first valve configured to control flow of the infusion fluid from the cassette infusion connector, (b) a second valve configured to control flow of the first ophthalmic substance from the first substance chamber, and (c) a third valve configured to control flow of the second ophthalmic substance from the second substance chamber where at least two of the first, second, and third valves may provide an alternative or mixed flow to the infusion cannula. In an alternative embodiment, the at least one valve may consist of one valve where the one valve is coupled to the cassette infusion connector, the first substance chamber, and the second substance chamber to control flow of the infusion fluid, the first ophthalmic substance, and the second ophthalmic substance to the infusion cannula.

In some embodiments, a method of ophthalmic substance delivery may comprise: providing infusion fluid through an infusion line to an infusion cannula, receiving a command to control a valve coupled to a substance chamber, and activating the valve to release an ophthalmic substance from the substance chamber into the infusion line to the infusion cannula. In some embodiments, activating the valve to release the ophthalmic substance from the substance chamber into the infusion line may result in a mixed flow of the infusion fluid and the ophthalmic substance to the infusion cannula. In some embodiments, the method may further include deactivating the infusion fluid flow to the infusion cannula prior to releasing the ophthalmic substance from the substance chamber and then deactivating the release of the ophthalmic substance prior to re-providing the infusion fluid to result in an alternating flow of the infusion fluid or the ophthalmic substance to the infusion cannula.

BRIEF DESCRIPTION OF THE DRAWINGS

The accompanying drawings illustrate embodiments of the devices and methods disclosed herein and together with the description, serve to explain the principles of the present disclosure.

Figure 1A:
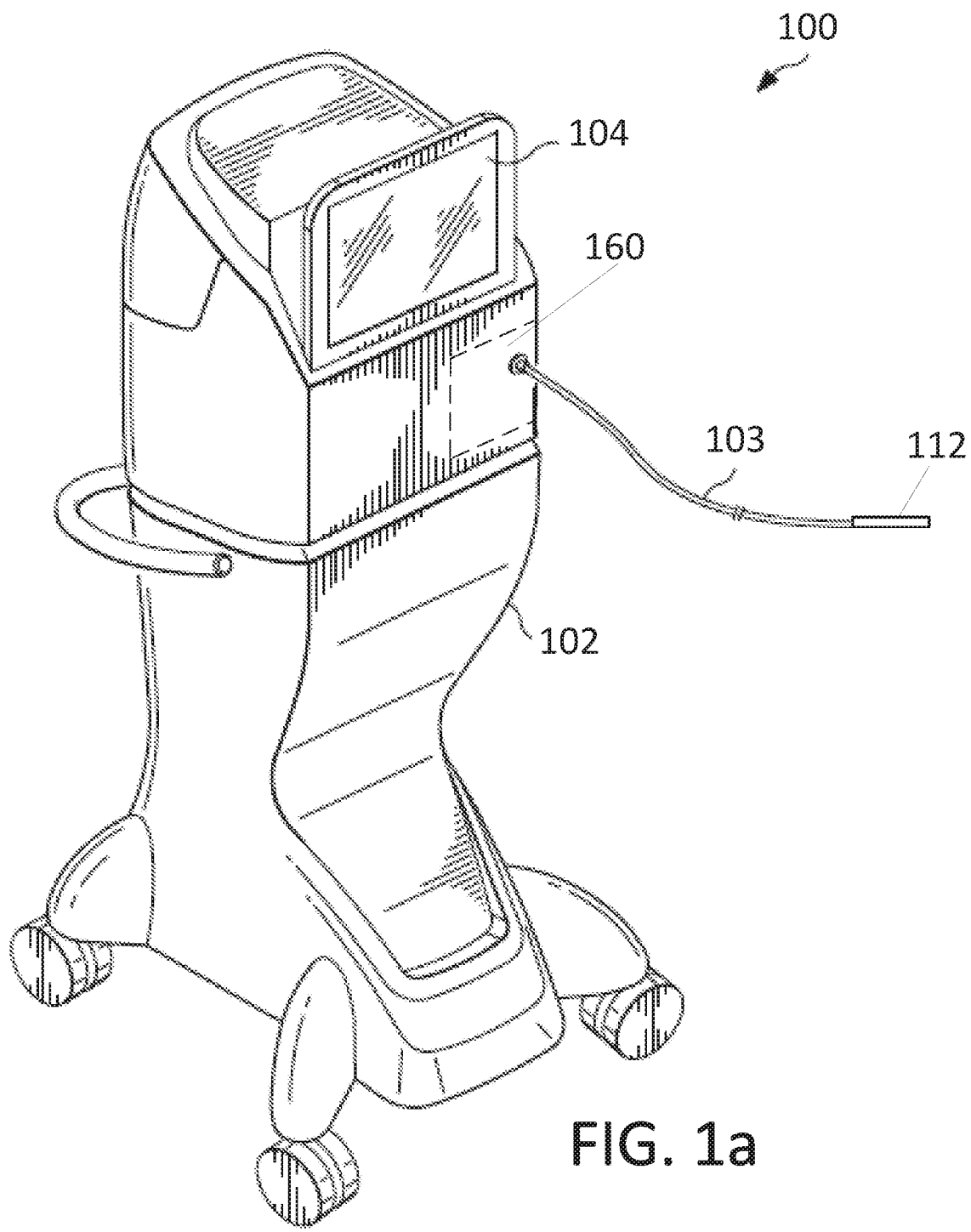
FIG. 1a illustrates a perspective view of an exemplary surgical system showing an infusion cannula connected by a single fluid line, according to an embodiment consistent with the principles of the present disclosure.

The accompanying drawings may be better understood by reference to the following detailed description.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or operations described with respect to one embodiment may be combined with the features, components, and/or operations described with respect to other embodiments of the present disclosure. For simplicity, in some instances the same reference numbers are used throughout the drawings to refer to the same or like parts. It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the accompanying drawings and the following detailed description.

The surgical system disclosed may provide infusion fluid and an ophthalmic substance (such as a dye, drug, or retina patch) through an infusion cannula into a body cavity. A separate incision/cannula may not be needed for the ophthalmic substance because the ophthalmic substance may be provided into the body cavity through the infusion cannula that is already providing infusion fluid. For example, a surgeon may perform a procedure that includes removal of vitreous from the eye using a vitrectomy probe and an infusion cannula (to supply infusion fluid to replace the volume of vitreous removed by the vitrectomy probe). The same infusion cannula may then be used to introduce an ophthalmic substance into the eye (e.g., alternately or simultaneously with the infusion fluid). Accordingly, a surgeon or other user may be able to supply infusion fluid and an ophthalmic substance into the vitreous chamber of the eye of the patient using one infusion cannula without requiring a separate incision or cannula.

FIG. 1a illustrates a perspective view of an exemplary surgical system, generally designated 100, according to an exemplary embodiment. The surgical system 100 may include a console 102 and an infusion cannula 112. The console 102 may include an associated display screen 104 configured to show data relating to system operation and performance during a surgical procedure (e.g., a vitrectomy). In some embodiments, the console 102 may be mobile and may include wheels to facilitate movement about an operating room. In an alternative embodiment, the console 102 may not include wheels. The console 102 may be referred to as a "base housing" and may include a plurality of subsystems that cooperate to enable a surgeon to perform a variety of surgical procedures, such as ophthalmic surgical procedures.

Figure 1B:
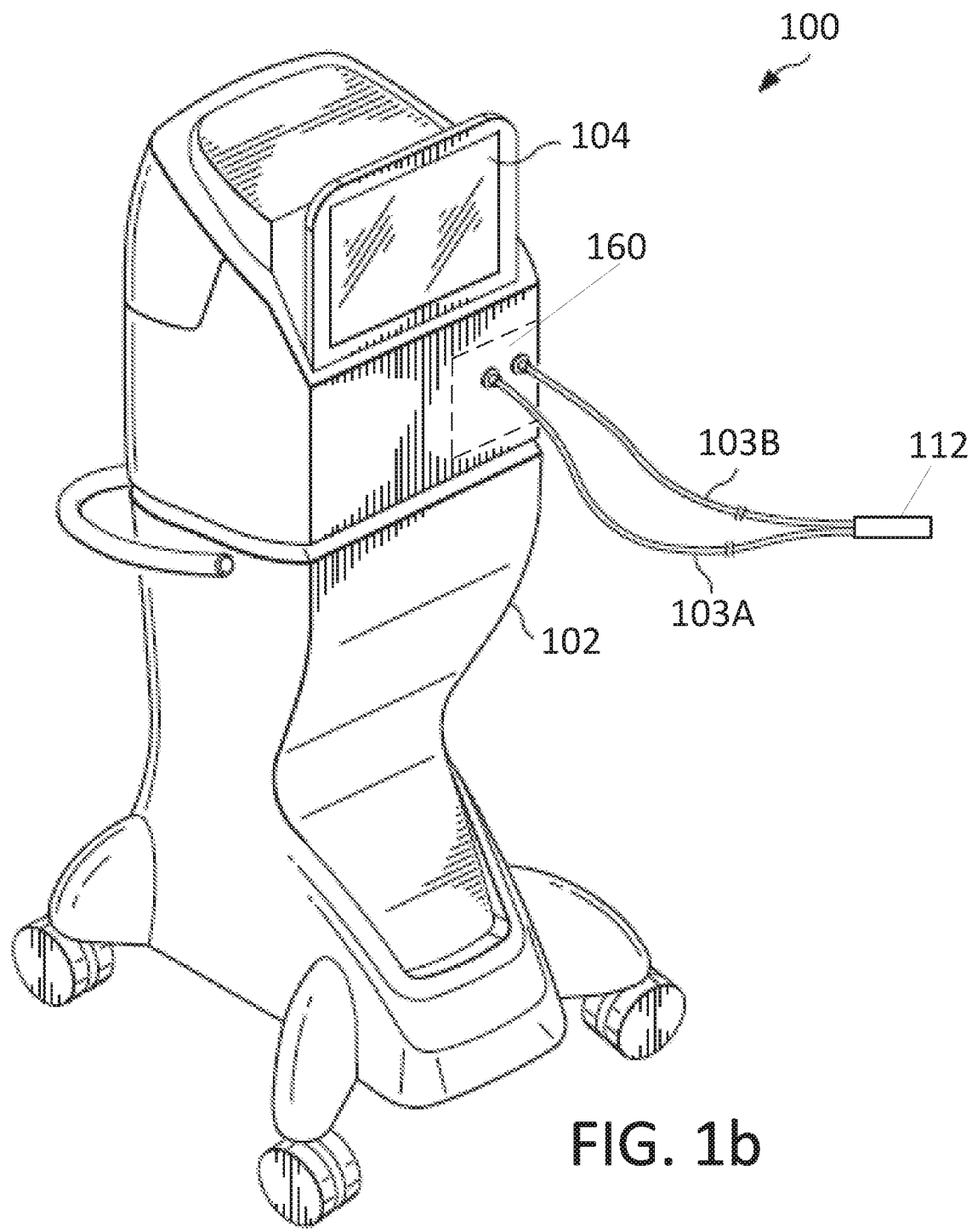
FIG. 1b illustrates a perspective view of an exemplary surgical system showing an infusion cannula connected by two fluid lines, according to an embodiment consistent with the principles of the present disclosure.

During an ophthalmic surgical procedure, an infusion cannula 112 may be used to provide infusion fluid to a surgical site. The infusion cannula 112 may have a distal end configured for insertion through eye tissue into the vitreous chamber of an eye. The infusion cannula 112 may have a short length such that the cannula extends just past the incision or may have a longer length (e.g., as part of a probe) such that the infusion fluid is provided closer to the back of the eye. The infusion cannula 112 may also take the form of an infusion sleeve on a phacoemulsification handpiece to provide infusion fluid during a cataract procedure. The infusion cannula 112 may fluidically coupled to the console 102 (e.g., connected directly to the console 102 or be indirectly connected to the console 102 through a cassette 160 loaded on the console 102) through one or more connection conduits (referred to collectively herein as "103"). In some implementations, the connection conduit 103 may be formed of one or more lengths of tubing (e.g., a length of tubing fluidically coupling the infusion cannula 112 to the cassette 160). The infusion cannula 112 may be coupled to the console 102 through a single connection conduit 103 (e.g., see FIG. 1a) or multiple connection conduits (e.g., connection conduits 103a and 103b shown in FIG. 1b). In some embodiments, the connection conduit 103 may themselves include a single lumen or may each include a plurality of lumens enabling multiple fluids to be conveyed to the infusion cannula 112. The surgical system may also use other conduits to convey, for example, other fluids (such as air, saline, removed vitreous, or ophthalmic substances), supply high and low fluid pressures (e.g., alternating air pressures to drive a vitrectomy probe), and provide electrical power and control signals.

Figure 2:
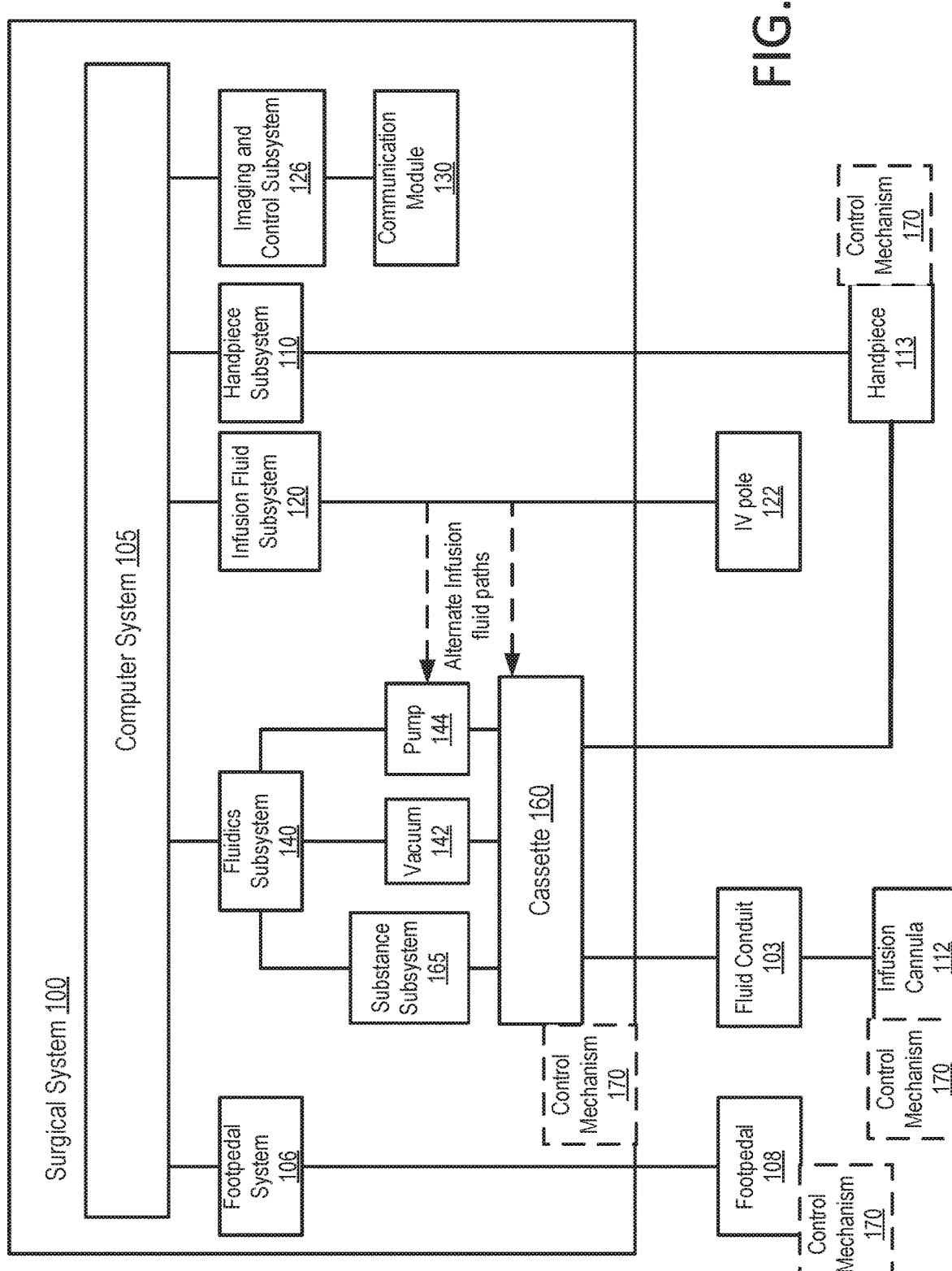
FIG. 2 is an illustration of an exemplary block diagram of the surgical system of FIG. 1, according to an aspect consistent with the principles of the present disclosure.

FIG. 2 is a block diagram of the surgical system 100 (which may be part of console 102) and several subsystems thereof. The surgical system 100 includes a computer subsystem 105, a display screen 104, and a number of subsystems that are used together to perform ocular surgical procedures, such as emulsification or vitrectomy surgical procedures, for example. The computer subsystem 105 may operate or control the subsystems according to instructions to provide proper operation of the subsystems. The computer subsystem 105 may include one or more processing devices, such as a central processing unit or a central processor or a microcontroller, and an information and data storage system. The data storage system may include one or more types of memory, such as RAM (random access memory), ROM (read-only memory), flash memory, a disk-based hard drive, and/or a solid-state hard drive. The processing devices and storage system may communicate over a bus, which may also permit communication with and between one or more of the plurality of subsystems of the surgical system 100.

In the exemplary implementation of FIG. 2, the subsystems include a footpedal subsystem 106 including, for example, a footpedal 108. The subsystems also include a fluidics subsystem 140 including an aspiration vacuum 142 and an infusion/irrigation pump 144 that couple to respective fluid conduits (e.g., directly or indirectly through a cassette 160)). In some embodiments, the fluid conduits may include one or more tubes extending between the console 102 and, for example, the handpiece 113 and infusion cannula 112. The surgical system 100 may further include a handpiece subsystem 110 with the handpiece 113. In addition to conveying, for example, aspiration (from aspiration vacuum 142) and power to the handpiece 112, the handpiece subsystem 110 may receive and/or encode signals to and from the handpiece 113 for communication between the handpiece 113 and the computer subsystem 105. The signals may enable the surgeon to use the handpiece 113 to control different subsystems (e.g., the substance subsystem 165) in the surgical system 100.

The surgical system 100 may further include an imaging and control subsystem 126 including a communication module 130. Other subsystems or tools may be included additionally or alternatively in other embodiments. For example, some embodiments may include a fiber optic illumination subsystem to provide for illumination within a body cavity, such as the vitreous chamber or anterior chamber of an eye. To optimize performance of the different subsystems during surgery, their operating parameters differ according to, for example, the particular procedure being performed, the different stages of the procedure, the surgeon's personal preferences and commands, whether the procedure is being performed in the anterior or posterior portion of the patient's eye, and so on.

The different subsystems in the console 102 may include control circuits for the operation and control of the respective microsurgical instruments or instrument components. The computer subsystem 105 governs the interactions and relationships between the different subsystems to properly perform an ocular surgical procedure and to properly communicate information to the operator of the surgical system 100 through the display 104 and/or through a coupled microscope or wearable computing device. In some implementations, the processing devices of the computer subsystem 105 are preprogrammed with instructions for controlling the subsystems to carry out a surgical procedure, such as an emulsification procedure or a vitrectomy, for example.

In addition, the console 102 may include one or more input devices that permit a user to make selections to control or modify the preprogrammed relationships between different subsystems. In this embodiment, input devices may be incorporated into the console and may include the footpedal 108, a touch screen device responsive to selections made directly on the screen, a standard computer keyboard, a standard pointing device, such as a mouse or trackball, buttons, knobs, or other input devices are also contemplated. For example, the handpiece 113 may include one or more switches, knobs, touch-sensors, sliders, or other input devices, to enable a user to use the handpiece 113 as an input device as well. Using the input devices, a surgeon, scientist, or other user may select or adjust parameters that affect the relationships between the different subsystems of the console 102.

The surgical system 100 may also include an infusion fluid subsystem 120 to supply infusion fluid to, for example, the infusion cannula 112 and/or handpiece 113. The infusion fluid subsystem 120 may include an intravenous (IV) pole subsystem including a motorized IV pole 122. In some embodiments, the infusion fluid subsystem 120 may not include an IV pole subsystem and IV pole, but instead the infusion fluid subsystem 120 may include an infusion fluid bag in a squeeze chamber (or, for example, a pressurized bottle). In some embodiments, the infusion fluid subsystem 120 may supply the infusion fluid 309 to the cassette 160 through a cassette infusion fluid connector 150 (see FIG. 3a) or may supply the infusion fluid 309 directly to the fluid conduit 103 (e.g., plastic tubing). In some embodiments, the infusion fluid 309 may be pumped through pump 144 into the cassette infusion fluid connector 150 (or pumped directly into the fluid conduit 103). Infusion fluid 309 may pass through the fluid conduit 103 into the infusion cannula 112. The infusion cannula 112 may have an inner lumen extending therethrough to deliver the infusion fluid 309 into the surgical site (e.g., into the vitreous chamber of the eye).

In some embodiments, the surgical cassette 160 may also include (or be coupled to) a substance subsystem 165 and one or more substance chambers 124 to provide one or more ophthalmic substances 305 (e.g., a visualization dye, a drug, retina patch, etc.) to the infusion cannula 112 through the first fluid conduit 103a (or second fluid conduit 103b). As seen in FIGS. 3a-5, the substance subsystem 165 may control ophthalmic substance delivery by, for example, controlling one or more valves 301 (referred to collectively herein as "301"). The substance line 125 may conduct the ophthalmic substance 305 from a substance chamber 124 to valve 301. The substance chamber 124 containing the ophthalmic substance 305 may be internal to the console 102/cassette 160 or may be external to the console 102/cassette 160 (e.g., as a pack/bottle coupled to the fluid conduit 103 or infusion cannula 112). In some embodiments, the substance line 125 may include, for example, an internal passageway in the cassette 160 (e.g., a molded plastic passageway formed between two cassette halves). In some embodiments, the substance line 125 may include a tubing or other fluid conduit. As discussed further below, the valve 301 may be used to control an amount, rate, etc. of the ophthalmic substance 305 to be provided to the infusion cannula 112.

In some embodiments, the valve 301 may provide an alternating flow of infusion fluid 309 or ophthalmic substance 305 to the infusion cannula 112 (e.g., one at a time to the infusion cannula 112). In some embodiments, the valve 301 may provide a mixed flow of infusion fluid 309 and ophthalmic substance 305 to the infusion cannula 112 (e.g., a combined flow with mixture of infusion fluid and ophthalmic substance such as a dye and an infusion fluid 309).

The mixture may be in a ratio designated by the user (or, for example, preprogrammed in the console). The alternate or mixed flow may be provided to the infusion cannula 112 through a fluid conduit 103 (which may be a tubing located between the console 102 and the infusion cannula 112). In another embodiment, as seen in FIG. 3b, the cassette 160 may be coupled to the infusion cannula 112 through a first fluid conduit 103a (to deliver the infusion fluid 309) and a second fluid conduit 103b (to deliver the ophthalmic substance 305).

The control mechanism 170 may include user controls located on or coupled to the surgical cassette 160 and/or the surgical console 102 (such as a footpedal 108, handpiece 113, display 104, connected thereto) to receive input (e.g., from a surgeon) to control supply an ophthalmic substance 305 from the substance chamber 124 through the infusion cannula 112. The control mechanism 170 may include, for example, a switch, button, slider, or roller (e.g., on a footpedal 108, handpiece 113, or an exterior of the console). In some embodiments, the control mechanism 170 may include a displayed graphical user interface. The control mechanism 170 may enable a surgeon to controllably provide a desired amount, rate, etc. of the ophthalmic substance 305 into the surgical site without removing the infusion cannula 112 from the site. For example, a surgeon may trigger introduction of an ophthalmic substance 305 from the substance chamber 124 through the infusion cannula 112 into the patient's eye. Additionally, a surgeon may change one or more parameters (such as aspiration or reflux parameters or an oscillation parameter of a vitreous cutting mechanism) for the operation of equipment coupled to the surgical console 102 (e.g., handpiece 113).

In some embodiments, input from a control mechanism 170 may be used to control ophthalmic substance delivery. FIG. 2 illustrates several possible locations for the control mechanism 170 (which are placed in dashed boxes to indicate that different locations are possible). For example, in some implementations the surgeon may activate a control mechanism 170 on the handpiece 113, on the footpedal 108, or the console 102 (e.g., as part of the cassette 160, display 104, or other location on the console 102) in order to provide the ophthalmic substance 305 at the desired location through the infusion cannula 112. In some embodiments, the handpiece 113 may include a control mechanism 170 such as a control wheel or selector wheel that may be manipulated by a finger or thumb of the surgeon during a procedure. Other control mechanisms 170 may be included in addition to the selection wheel or in place thereof. Such control mechanisms 170 may include buttons, switches, etc. In some embodiments, the control mechanism 170 may be implemented through a Graphical User Interface on a touchscreen (e.g., display 104).

Figure 3A:
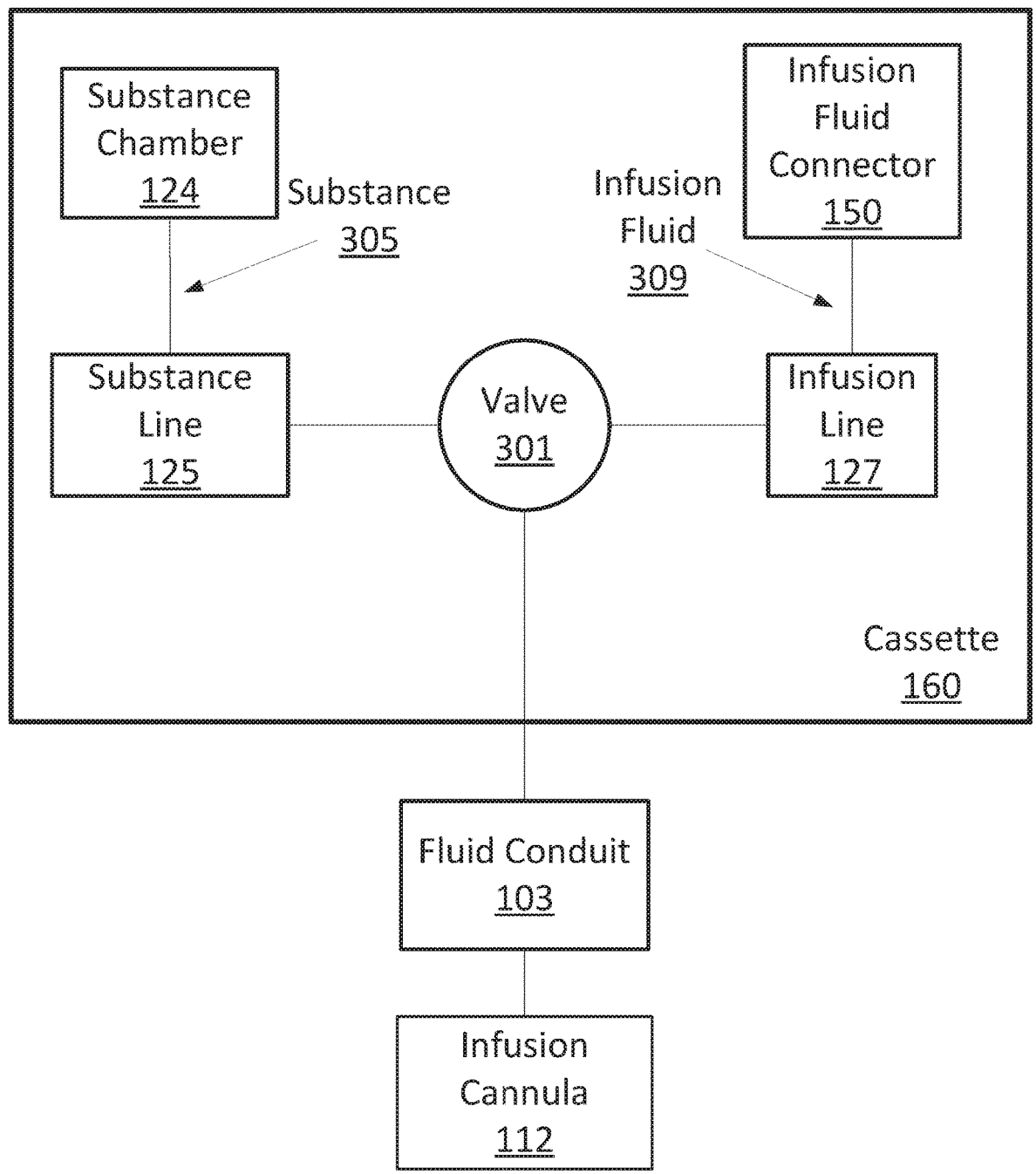
FIG. 3a is a cross-sectional illustration of an exemplary surgical cassette coupled to an infusion cannula, according to aspects of the present disclosure.
Figure 3B:
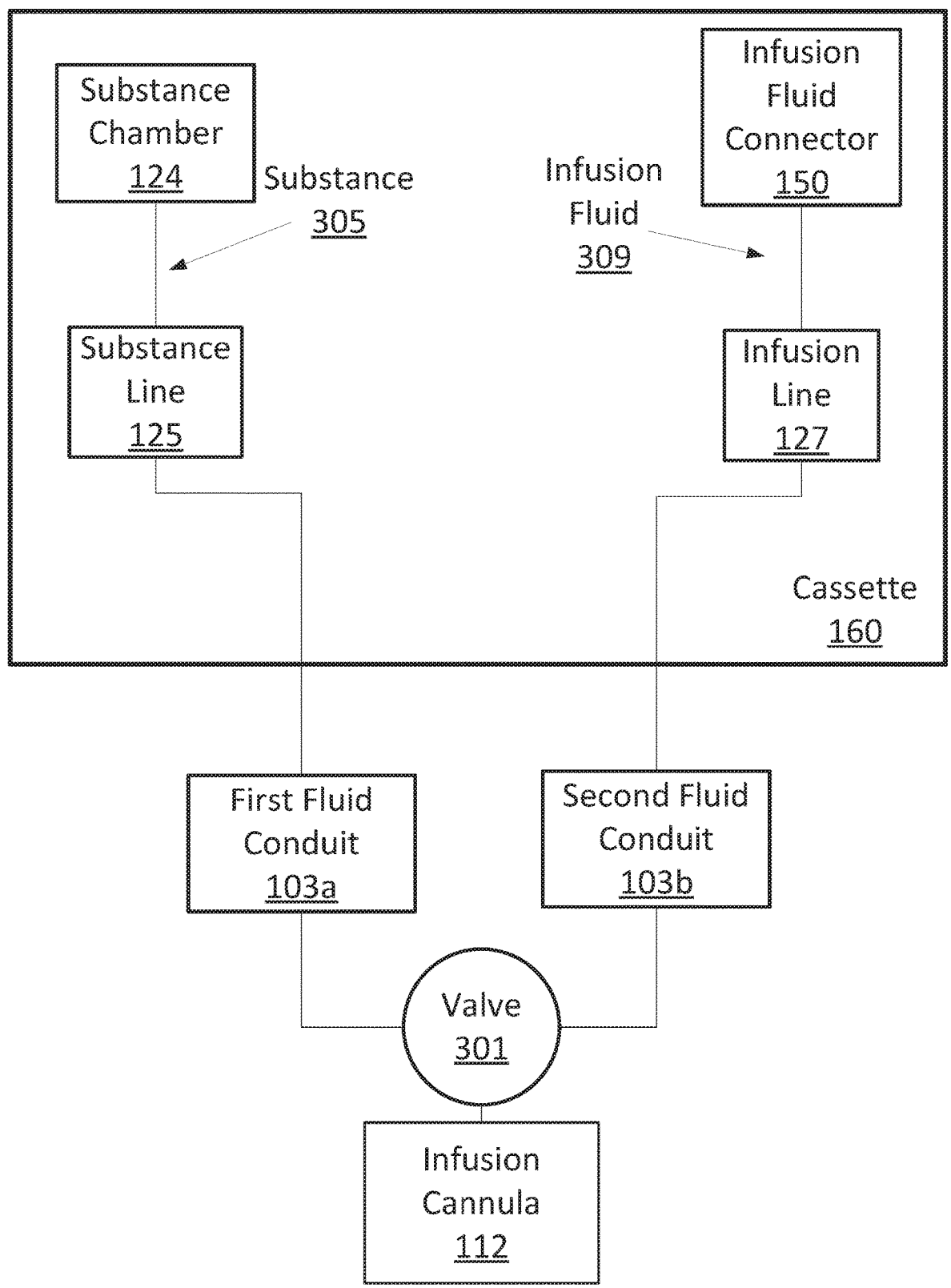
FIG. 3b is a cross-sectional illustration of an exemplary surgical cassette coupled to an infusion cannula through two fluid conduits, according to aspects of the present disclosure.

FIG. 3a depicts a substance chamber 124 that is coupled to the infusion cannula 112 through a valve 301 and a fluid conduit 103 (e.g., a tubing). A cassette infusion fluid subsystem 120 may also be coupled to the valve 301 (e.g., through infusion fluid connector 150) to provide infusion fluid 309 to the infusion cannula 112. When a volume of ophthalmic substance 305 is to be provided from the substance chamber 124 or the cassette infusion fluid subsystem 120, another fluid, such as air, may be pushed into the respective substance chamber 124 or infusion fluid bag to pressurize the ophthalmic substance 305 or infusion fluid 309 against the valve 301. In some embodiments, the substance 305 or infusion fluid 309 may flow because of gravity (e.g., the infusion fluid subsystem 120 may include an IV pole 122 and bag). In some embodiments, the valve 301 may alternate between the substance chamber 124 and the cassette infusion fluid system 120. In some embodiments, the valve 301 may allow an ophthalmic substance 305 and the infusion fluid 309 to flow through the valve 301 at the same time in a mixed flow. In some embodiments, different positions of the valve 301 may control the ratio of ophthalmic substance 305 to infusion fluid 309 flowing through the valve 301. In some embodiments, the valve 301 may also have an off position that prevents flow from the substance chamber 124 and the cassette infusion fluid system 120.

As shown in FIG. 3a, the valve 301 and the substance chamber 124 may be located in the cassette 160. Other locations of the valve 301 and the substance chamber 124 are also contemplated. For example, the valve 301 and the substance chamber 124 may be located along the fluid conduit 103 between the cassette 160 and the infusion cannula 112. In some embodiments, the valve 301 may be located in the infusion cannula 112 and a line 103a from a cassette infusion fluid system 120 and a line 103b from a substance chamber 124 may extend from the console 102 to the infusion cannula 112 (see FIG. 1b).

In some embodiments, the valve 301 may be responsive to commands received from the console 102 (e.g., commands sent by the console 102 in reaction signals from the control mechanism 170). In some embodiments, the commands may control which ophthalmic substance 305 or infusion fluid 309 to supply. The commands may further control an amount, rate, volume, etc. of the ophthalmic substance 305 or infusion fluid 309 to supply (e.g., by controlling the timing of the valve activation). For example, the user may use one or more touchscreen graphical objects to turn the dye on/off, increase/decrease rate, set an amount of dye to release, etc. In some embodiments, the control mechanism 170 may include an encoder that generates electronic signals that are transmitted to the console 102. The computer subsystem 105 may receive the control signals and communicate the signals to, for example, the fluidics subsystem 140 which may be used to electrically control the state (open, closed, or another position therebetween) of the valve 301. In some embodiments, the valve 301 may be directly controllable in response to user input to a control mechanism 170 (e.g., pressing a button on a vitrectomy probe, infusion cannula 112, cassette 160, or console 102). As another example, a slider on the handpiece or infusion cannula 112 may directly control the valve 301. Other control mechanisms 170 are also contemplated (e.g., depressing foot pedal 108).

Figure 4:
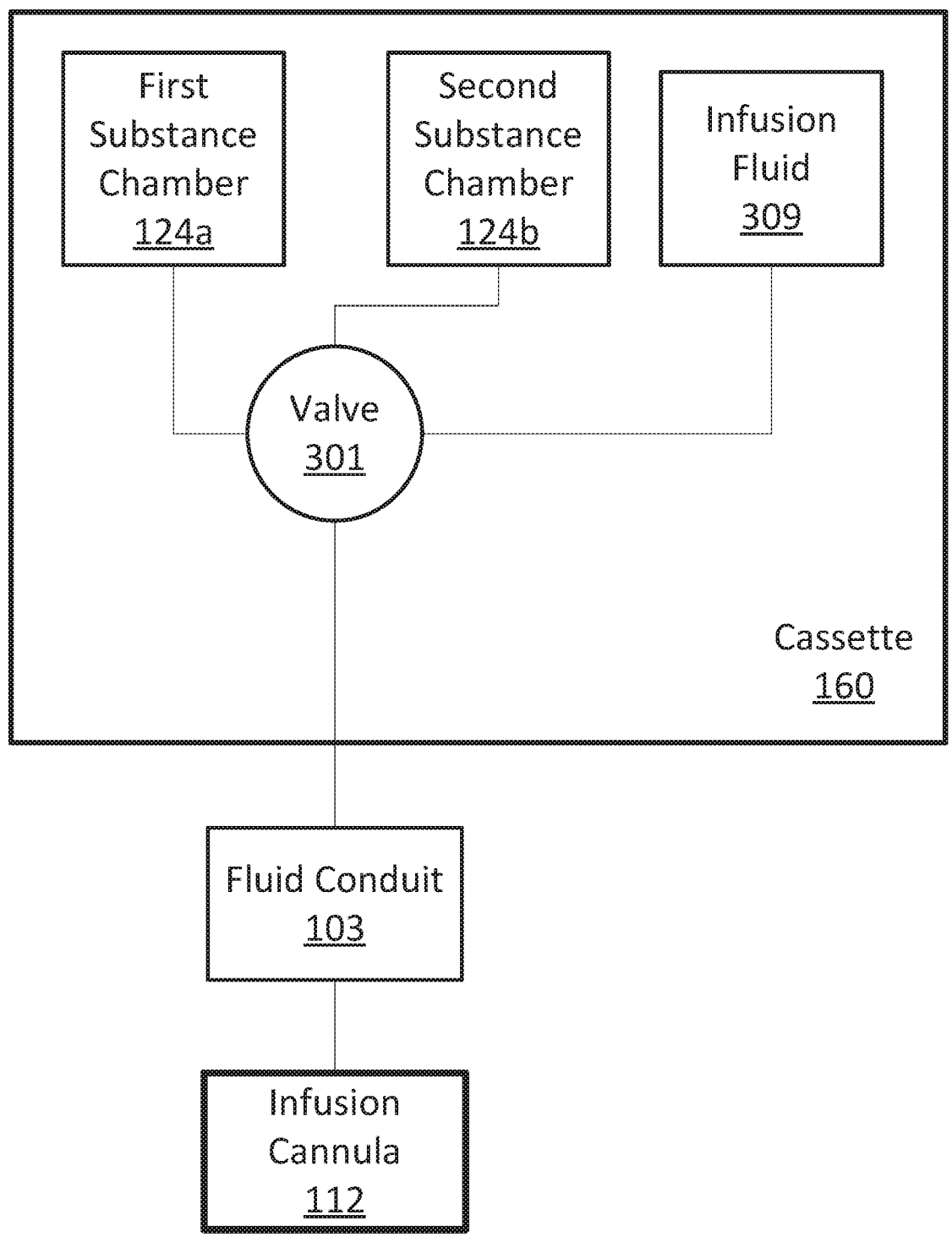
FIG. 4 shows a block diagram representation of a cassette having two substance chambers accessible to the infusion cannula through one valve, according to aspects of the present disclosure.

As seen in FIG. 4, in some embodiments, two or more substance chambers 124 may be connected to the valve 301. Two substance chambers 124a,b are shown (e.g., one chamber 124a with a dye and one chamber 124b with a drug), but any number of substance chambers (referred to collectively herein as 124) may be used. In some embodiments, valve 301 may allow many different pathways for directing ophthalmic substances 305 and infusion fluid 309 to the infusion cannula 112 (e.g., valve 301 may be a rotary valve with multiple pathways). In one orientation, valve 301 may direct an ophthalmic substance 305 from one or more substance chambers 124 to the infusion cannula 112 while blocking infusion fluid 309. In another orientation, the valve 301 may instead direct infusion fluid 309 to the infusion cannula 112 while blocking ophthalmic substances 305 from the substance chambers 124 from being sent to the infusion cannula 112. In yet another orientation, the valve 301 may direct a mixture of ophthalmic substances 305 (from one or more substance chambers 124) and infusion fluid 309 in a mixed flow to the infusion cannula 112. The mixture may be in a ratio designated by the user (or, for example, preprogrammed in the console). In an off configuration, the valve 301 may prevent any ophthalmic substance 305 or infusion fluid 309 from being sent to the infusion cannula 112. Other configurations and valve types are also possible.

Figure 5:
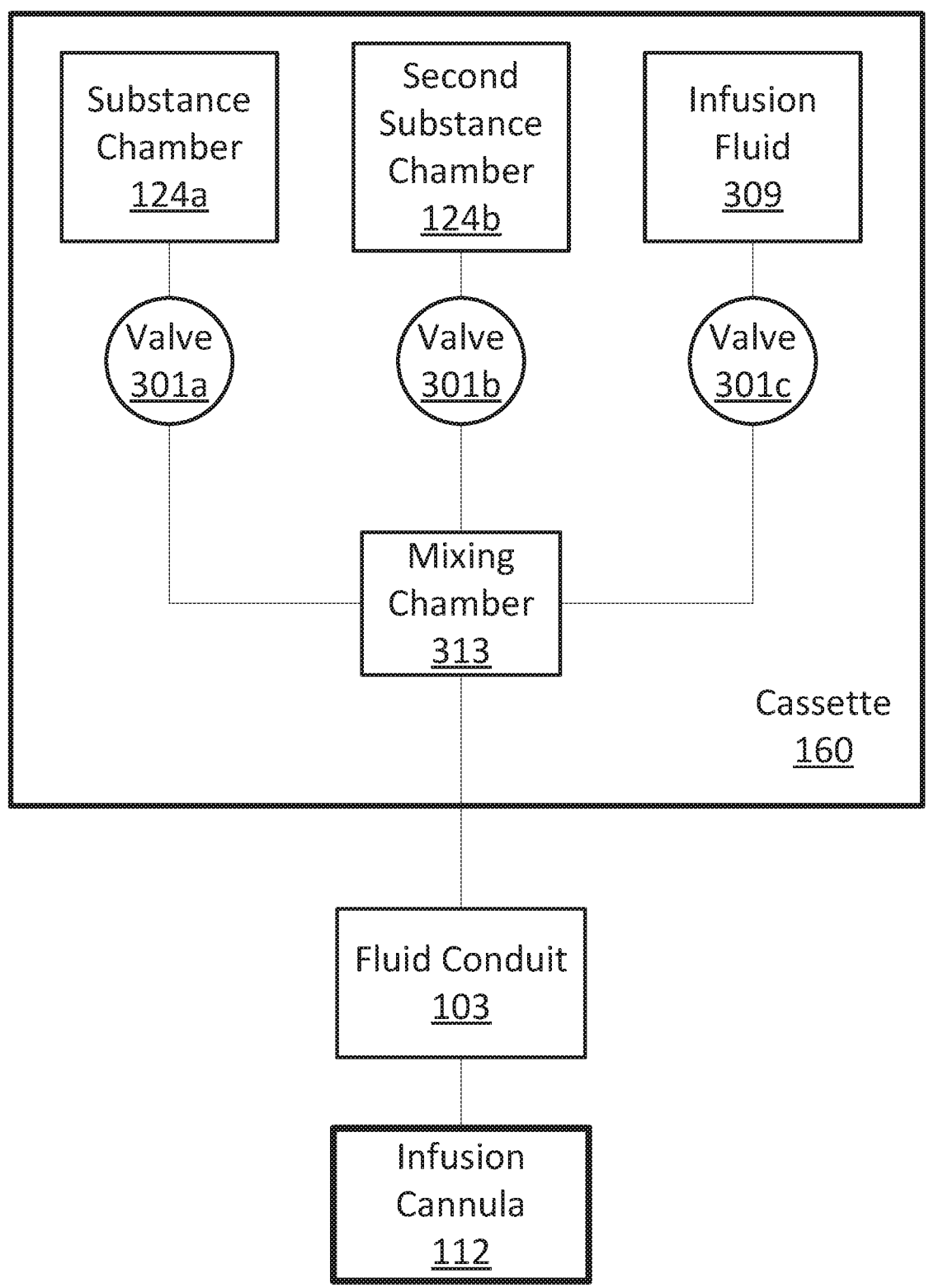
FIG. 5 shows a block diagram representation of a cassette having two substance chambers accessible to the infusion cannula through separate valves, according to aspects of the present disclosure.

FIG. 5 illustrates an embodiment with multiple valves 301a,b,c (referred to collectively herein as 301) directing flows into a mixing chamber 313. As seen in FIG. 5, each chamber may have a separate valve to control the flow of an ophthalmic substance 305 (or infusion fluid 309) from the respective chamber. In some embodiments, the output of the valves 301 may mix in a mixing chamber 313 prior to entering the fluid conduit 103 and infusion cannula 112. In some embodiments, there may be an additional valve between the mixing chamber 313 and the infusion cannula 112. Similar to the discussion of valve 301 with respect to FIG. 3a above, the various valves 301 may be controlled indirectly or directly by control mechanism 170 (e.g., through signals directly from control mechanism 170 or indirectly by receiving signals from the console 102 (which may receive signals from the control mechanism 170)).

Figure 6:
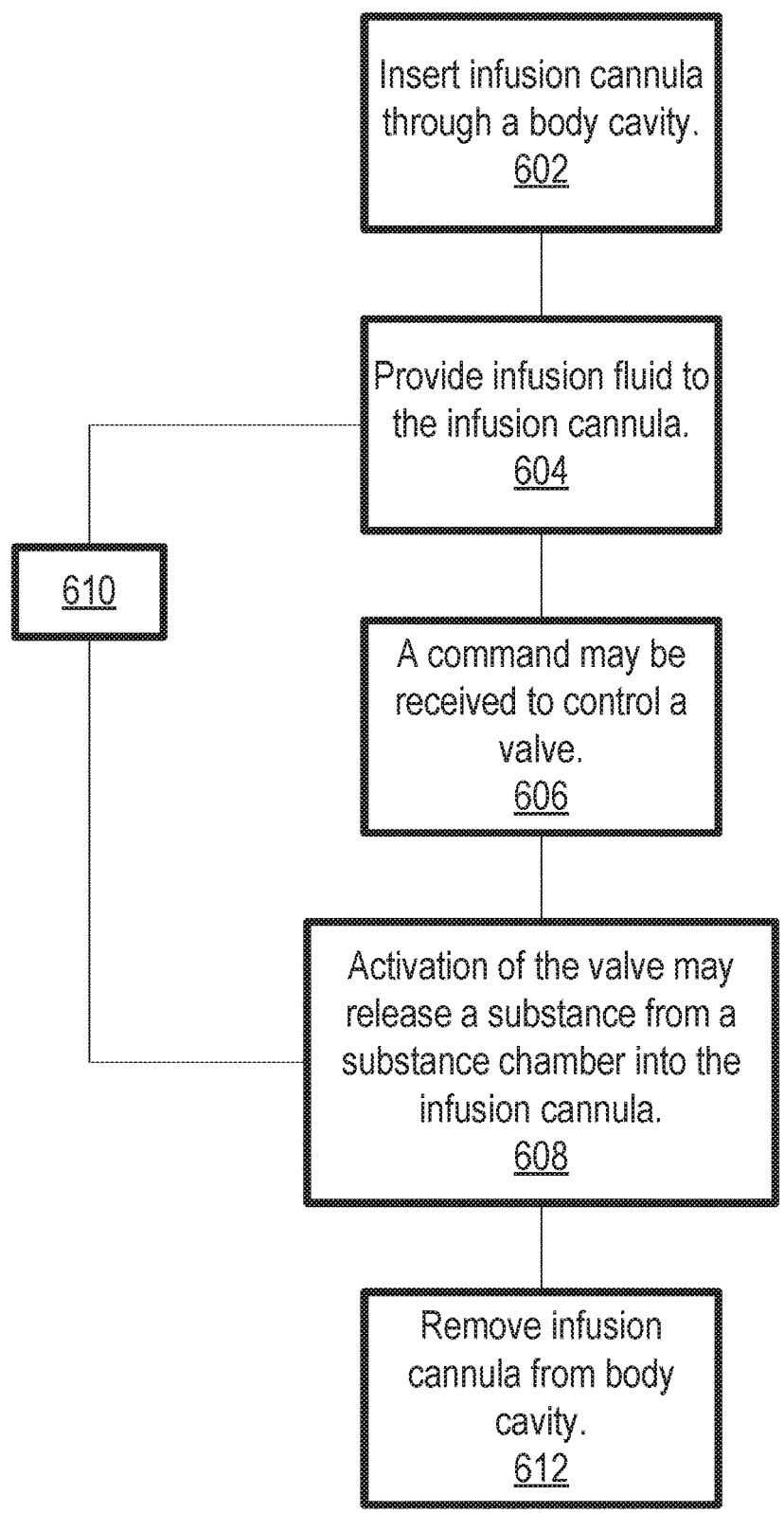
FIG. 6 shows a block diagram of a method for dispensing infusion fluid and an ophthalmic substance through the infusion cannula, according to aspects of the present disclosure.

Referring now to FIG. 6, shown therein is a method 600 of performing a surgical procedure to remove tissue from a surgical site. As illustrated in FIG. 6, the method 600 includes a plurality of enumerated operations. Embodiments of the method 600 may include additional operations before, after, in between, or as part of the enumerated operations. Additionally, some embodiments of the method 600 may not include all of the illustrated operations. One or more of the operations may be provided as instructions, stored on a computer readable media that may be executed by a computer system like the computer subsystem 105 of FIG. 2.

As shown in FIG. 6, an embodiment of the method 600 may include performing a surgical procedure (e.g., a posterior segment procedure) using a surgical device. In some embodiments, a surgeon may make an incision in the eye of a patient. At 602, the surgeon may insert the infusion cannula 112 through the incision and into the eye. In some embodiments, a separate cannula may be positioned in the incision and the infusion cannula 112 may be placed into the separate cannula to access the eye. In some embodiments, the incision may be made as the separate cannula is inserted (instead of prior to the cannula's insertion). In some embodiments, additional instruments (e.g., a vitreous cutter) may be inserted into the eye through additional incisions/cannulas.

At 604, an infusion fluid 309 may be provided to the infusion cannula 112 (e.g., as part of a vitreous removal procedure). During parts of the procedure, the valve 301 may allow only the infusion fluid 112 (e.g., Balanced Salt Solution (BSS®)) to flow through to the infusion cannula 112.

At 606, a command may be received from a control mechanism 170 to control a valve 301 (or plurality of valves 301). In some embodiments, the valve 301 may be responsive to commands (e.g., control signals) received from the control mechanism 170 (e.g., either directly or indirectly). In some embodiments, the console 102 may receive control signals from the control mechanism 170 and electrically control the state (open, closed, or another position therebetween) of the valve 301. In some embodiments, the control mechanism 170 may include a graphical user interface or a user control on a handpiece, etc. to release ophthalmic substance 305 from the substance chamber 124. In some embodiments, the valve 301 may be directly controllable in response to user manipulations of a control mechanism 170 (e.g., on the handpiece 113, foot pedal 108, infusion cannula 112, cassette 160, or console 102). For example, a slider on the infusion cannula 112 may directly control the valve 301. Other control mechanisms 170 are also contemplated.

At 608, activation of the valve 301 may release an ophthalmic substance 305 from a substance chamber 124 into the infusion cannula 112. The valve 301 may be moved to a position that allows ophthalmic substance 305 from the substance chamber 124 (or multiple substance chambers) to flow through to the infusion cannula 112. In some embodiments, the valve 301 may allow through only the ophthalmic substance 305 from the substance chamber 124 or may allow infusion fluid 309 and the ophthalmic substance 305 from the substance chamber 124 to flow through to the infusion cannula 112. The ophthalmic substance 305 may be, for example, a drug (e.g., a vitreous dissolution drug), a retina patch, or a dye (e.g., used to increase visibility of the tissue, particularly when the tissue is transparent or translucent, as is vitreous). Other ophthalmic substances 305 are also contemplated. If the ophthalmic substance is a dye, removal of vitreous may be simplified by allowing the dye to be more easily introduced, increasing the ability to visualize the vitreous during the removal procedure. This may also reduce the incidence of post-operative complications, including, for example, post-operative retinal tearing, retinal detachment, and other complications. If the ophthalmic substance is a dye, the surgeon may be able to better visualize aspects of the surgical operations performed by or near by the infusion cannula 112, without requiring two incisions and without requiring the manipulation and handling of two separate devices within the small confines of the eye or in another cavity or area of the patient.

As seen in FIGS. 4-5, in some embodiments, two or more substance chambers 124 may provide ophthalmic substances 305 to the infusion cannula 112 (e.g., one chamber with a dye and one chamber with a drug). The valve 301 may allow through a designated ratio of one or more of the substance chambers 124 and/or source of infusion fluid 120. For example, the ratio may be indicated by the user through the control mechanism 170. In some embodiments, the ophthalmic substance 305 may be delivered through the infusion cannula 112 separate from the infusion fluid 309 (e.g., the infusion fluid 309 may be discontinued prior to supplying the ophthalmic substance 305 to the infusion cannula 112). In some embodiments, the ophthalmic substances 305 and infusion fluid 309 may be delivered to the infusion cannula 112 through the same fluid conduit 103a or through separate fluid lines 103a,b. Activating the at least one valve to release the ophthalmic substance from the substance chamber into the infusion line may result in a mixed flow of infusion fluid 309 and ophthalmic substance 305 to the infusion cannula 112. In some embodiments, the flow of infusion fluid may be deactivated prior to releasing the ophthalmic substance 305 from the substance chamber and then deactivating the release of the ophthalmic substance 305 prior to re-providing the infusion fluid 112 to result in an alternating flow of infusion fluid 112 or ophthalmic substance 305 to the infusion cannula 112.

After the ophthalmic substance 305 has been released, at 610, some implementations of the method 600 may return to 604 at which only the infusion fluid 309 is released into the infusion cannula 112. The ophthalmic substance 305 may be released again as needed by the surgeon. At 612, the infusion cannula 112 may be removed from the body cavity. For example, after removing the desired amount of vitreous, the surgeon may remove the infusion cannula 112 from the vitreous chamber of the eye of the patient. Subsequent operations may be performed thereafter depending on the condition to be treated.

Through use of principles described herein, a user can deliver an ophthalmic substance 305, such as a drug, retina patch, dye, etc. into the eye as needed. In the case of a dye, the user may have a better experience when viewing tissue at the surgical site. Specifically, the user may be better able to visualize clear vitreous or other transparent or translucent tissue by introducing a dye that adheres to the tissue. The tissue may then be more readily removed. The integrated substance injector of tissue removal systems described herein may simplify the surgical procedure.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A cassette, comprising:
   a cassette infusion connector configured to receive infusion fluid from an infusion fluid system;
   a substance chamber comprising a substance;
   at least one valve coupled to the cassette infusion connector and the substance chamber;
   wherein the at least one valve is configured to control flow of the infusion fluid from the cassette infusion connector and control flow of the substance from the substance chamber, wherein a position of the valve controls a ratio of the substance to infusion fluid flowing through the valve to create a mixed flow;
   wherein the mixed flow from the at least one valve is provided to an infusion cannula fluidically coupled to the cassette.

2. The cassette of claim 1, wherein the substance in the substance chamber is an ophthalmic drug, a retina patch material, or an ophthalmic dye.

3. The cassette of claim 1, wherein the at least one valve is also configured to provide an alternating flow of the infusion fluid or the substance to the infusion cannula.

4. The cassette of claim 1, wherein the substance chamber is a first substance chamber comprising a first substance and wherein the cassette further comprises a second substance chamber comprising a second substance.

5. The cassette of claim 4, wherein the at least one valve is configured to control flow of the infusion fluid from the cassette infusion connector, the first substance from the first substance chamber and the second substance from the second substance chamber to provide an alternative or mixed flow to the infusion cannula.

6. The cassette of claim 4, wherein the at least one valve comprises:
   a first valve configured to control flow of the infusion fluid from the cassette infusion connector,
   a second valve configured to control flow of the first substance from the first substance chamber, and
   a third valve configured to control flow of the second substance from the second substance chamber,
   wherein at least two of the first, second, and third valves provide an alternative or mixed flow to the infusion cannula.

7. The cassette of claim 4, wherein the at least one valve consists of one valve, and wherein the one valve is coupled to the cassette infusion connector, the first substance chamber, and the second substance chamber to control flow of the infusion fluid, the first substance, and the second substance to the infusion cannula.

8. The cassette of claim 1, further comprising a control mechanism configured to receive input from a user, wherein the at least one valve is controlled by the control mechanism.

9. The cassette of claim 1, wherein the substance and infusion fluid are mixed as they travel through the valve and not before the substance and the infusion fluid enter the valve.

10. A system, comprising:
    a source of infusion fluid;
    a cassette, comprising:
    a cassette infusion connector configured to receive infusion fluid from the source of infusion fluid;
    a substance chamber comprising a substance;
    at least one valve coupled to the cassette infusion connector and the substance chamber, wherein the valve is configured to control flow of an infusion fluid from the cassette infusion connector and the substance from the substance chamber to provide a mixed flow to an infusion cannula, wherein a position of the valve controls a ratio of the substance to infusion fluid flowing through the valve to create the mixed flow; and
    a control mechanism configured to receive input from a user, wherein the at least one valve is controlled by the control mechanism to adjust the ratio according to the received input from the user.

11. The system of claim 10, wherein the substance in the substance chamber is an ophthalmic drug, a retina patch material, or an ophthalmic dye.

12. The system of claim 10, wherein the at least one valve is also configured to provide an alternating flow of the infusion fluid or the substance to the infusion cannula.

13. The system of claim 10, wherein the substance chamber is a first substance chamber comprising a first substance and wherein the cassette further comprises a second substance chamber comprising a second substance.

14. The system of claim 13, wherein the at least one valve is configured to control flow of the infusion fluid from the cassette infusion connector, the first substance from the first substance chamber and the second substance from the second substance chamber to provide an alternative or mixed flow to the infusion cannula.

15. The system of claim 13, wherein the at least one valve comprises:
    a first valve configured to control flow of the infusion fluid from the cassette infusion connector,
    a second valve configured to control flow of the first substance from the first substance chamber, and
    a third valve configured to control flow of the second substance from the second substance chamber,
    wherein at least two of the first, second, and third valves provide an alternative or mixed flow to the infusion cannula.

16. The system of claim 13, wherein the at least one valve consists of one valve, and wherein the one valve is coupled to the cassette infusion connector, the first substance chamber, and the second substance chamber to control flow of the infusion fluid, the first substance, and the second substance to the infusion cannula.

17. The system of claim 10, wherein the substance and infusion fluid are mixed as they travel through the valve and not before the substance and the infusion fluid enter the valve.

18. A method, comprising:
provide infusion fluid through an infusion line to an infusion cannula;
receiving a command to control a valve coupled to a substance chamber; and
activate the valve to release a substance from the substance chamber into the infusion line to the infusion cannula, wherein activating the valve comprises controlling a position of the valve to control a ratio of the substance to infusion fluid flowing through the valve to create a mixed flow.

19. The method of claim 18, further comprising deactivating the infusion fluid flow to the infusion cannula prior to releasing the substance from the substance chamber and then deactivating the release of the substance prior to re-providing the infusion fluid to result in an alternating flow of the infusion fluid or the substance to the infusion cannula.

20. The method of claim 18, wherein the substance and infusion fluid are mixed as they travel through the valve and not before the substance and the infusion fluid enter the valve.

\* \* \* \* \*